United States Patent
Ehsani et al.

(10) Patent No.: US 6,426,109 B1
(45) Date of Patent: Jul. 30, 2002

(54) METHOD OF TREATING COLOSTRUM

(75) Inventors: Neda Ehsani, Espoo; Ari Hemminki, Helsinki, both of (FI)

(73) Assignee: Novatreat Oy, Turku (FI)

( * ) Notice: Subject to any disclaimer, the term of this patent is extended or adjusted under 35 U.S.C. 154(b) by 0 days.

(21) Appl. No.: 09/577,335

(22) Filed: May 23, 2000

(30) Foreign Application Priority Data

May 25, 1999 (FI) .................................................. 991186

(51) Int. Cl.⁷ .............................................. A23C 21/00
(52) U.S. Cl. ...................... 426/580; 426/478; 426/490; 426/491; 426/583
(58) Field of Search ................................ 426/580, 583, 426/478, 490, 491; 210/634, 649, 650, 651; 530/365, 366

(56) References Cited

U.S. PATENT DOCUMENTS

| | | |
|---|---|---|
| 3,911,108 A | 10/1975 | Singh |
| 4,140,806 A | 2/1979 | Glimenius et al. |
| 4,644,056 A | 2/1987 | Kothe et al. |
| 4,784,850 A | 11/1988 | Abraham |
| 5,028,436 A | 7/1991 | Gauri |
| 5,147,548 A | 9/1992 | Hies et al. |
| 5,256,437 A | 10/1993 | Degen et al. |
| 5,670,196 A | 9/1997 | Gregory |
| 5,683,733 A | 11/1997 | Krabsen et al. |
| 5,707,678 A | 1/1998 | Gregory |

FOREIGN PATENT DOCUMENTS

| | | |
|---|---|---|
| DE | 196 19 990 A1 | 11/1997 |
| EP | 0 334 776 A3 | 9/1989 |
| GB | 1 573 995 | 3/1978 |
| WO | 86/01687 | 3/1986 |
| WO | 95/10192 | 4/1995 |
| WO | 97/16977 | 5/1997 |
| WO | 99/55168 | 11/1999 |

*Primary Examiner*—Leslie Wong
(74) *Attorney, Agent, or Firm*—Nixon & Vanderhye P.C.

(57) ABSTRACT

A method for treating colostrum to reduce the bioburden while retaining a high active protein content is described. The method is especially useful for recovering maximum immunoglobulin activity. The colostrum treated by the method is useful in the manufacture of clinical nutritive preparation, functional foods and food supplements.

11 Claims, No Drawings

METHOD OF TREATING COLOSTRUM

FIELD OF THE INVENTION

The present invention relates to a method for recovery of bioactive colostrum components. More precisely the present invention is directed to a method for treating colostrum to reduce the bioburden while retaining a high active protein content. The invention is also directed to the colostrum treated by said method and to the use thereof.

BACKGROUND OF THE INVENTION

Milk produced just after parturition is called colostrum. This particular milk contains about 20 times more protein than milk produced later. Colostrum is, therefore, an excellent source of many valuable proteins, such as biologically active proteins like growth factors and especially immunoglobulins. The colostrum can, therefore, be used as a source of said valuable proteins e.g. in food or clinical preparations. However, colostrum is often contaminated with a high amount of bacteria and other cell material, which is not allowed in a product qualified as a food or clinical product.

The conventional way of reducing the bioburden of milk is pasteurization and ultra-heat treatment i.e. the milk is exposed to heat for a short period of time. However, the heat treatment does not only destroy the microorganisms present in the milk, but also denatures the valuable biologically active proteins. Colostrum is especially unsuitable for heat treatment, as the high protein content makes it coagulate at elevated temperatures. A method of reducing the bioburden of colostrum by centrifugation has been described in W097/16977. However, an effective reduction of bacteria requires such a high force of gravitation that proteins might precipitate together with other particles present in a protein rich solution.

Other methods of reducing microbial contaminants in milk are gamma radiation (U.S. Pat. No. 4,784,850) and treatment with β-propiolactone (U.S. Pat. No. 3,911,108). Also, these methods tend to denature proteins to some extent. Sterile filtration is still another method of removing microbes from milk (U.S. Pat. No. 5,256,437; U.S. Pat. No. 5,683,733; Pedersen P. J., (1991) IDF special issue no 9201. Microfiltration for the Reduction of Bacteria in Milk and Brine, In New Applications of Membrane Processes, 33–50; Osterland N., New Developments in Membrane Processing, IDF 25th International Dairy Congress Sep. 21–24, 1998 Århus, Denmark; and Rosenberg M. (1995), Trends in Food Science & Technology, 6:12–19). Filtration has also been used for separating different components in milk such as skim milk and cream-enriched fractions (U.S. Pat. No. 4,140,806), and dissolved and undissolved components in milk (U.S. Pat. No. 5,028,436). Filtration does not usually substantially affect the proteins, but the filters rapidly foul. This is especially a problem with protein rich colostrum, where the casein easily clogs the filters.

The problem with clogged filters has previously been solved by partially or completely removing casein from the colostrum, and/or by diluting the colostrum before filtration. Casein can be removed by either acid or enzymatic precipitation and centrifugation to obtain whey (U.S. Pat. No. 4,644,056 and GB 1,573,995). U.S. Pat. No. 5,670,196 discloses a method of microfiltrering colostrum, whereby defatted colostrum is first acidified to precipitate casein, which is removed by centrifugation, and then the whey is filtered through a charged depth filter to reduce the microorganism content. U.S. Pat. No. 5,707,678 is directed to a similar method, where casein is removed, after which the acidified whey is first ultrafiltered and then microfiltered. The main drawback of these methods is that large amounts of valuable antibodies and other proteins tend to precipitate together with the casein. In addition the removal of casein is a laborious, time consuming and expensive process.

U.S. 5,147,548 discloses a method of sterile-filtering colostrum without previously removing the casein. The optionally defatted colostrum is acidified to a pH of less than 3.5. The casein precipitates at a pH of 5 to 4, but it returns into solution as the pH continues to drop. The acidic solution was found to differ so extensively from the original colostrum that it could be sterile filtered either as such or after neutralizing it back to its original pH. The filter used is a depth filter or a membrane filter. In a preferred embodiment the colostrum is diluted into a sodium chloride solution prior to acidifying. However, also this method has drawbacks. The immunoglobulins are easily inactivated at low pH. Further, the casein precipitation is not fully reversible resulting also in protein loss, and the dilution of the colostrum increases process time and expenses.

The object of the present invention is to provide a simple, effective and economic method of reducing the bioburden of colostrum without substantially affecting the proteins contained therein. The method provides the elimination of microbial contaminants without substantial loss of the high and versatile biologically active protein content and/or activity. The method thus enables effective reduction of the bioburden while retaining the maximum immunoglobulin activity, especially IgG. No previous precipitation of casein nor any dilution, or addition of salts/acids/bases or other chemicals are needed, and there is no temperature denaturation of the antibodies present.

Another object of the invention is to provide a colostrum preparation of high hygienic standard, which qualifies as a food or clinical article. The colostrum preparation can be used in the form of a beverage or food or in dry form for promoting health or for treating or preventing disorders, which can be cured by immunoglobulins or additional colostrum proteins.

SUMMARY OF THE INVENTION

It has surprisingly been found, that a simple filtering system allows the reduction of the bioburden of colostrum without multistep pretreatment and loss of protein activity. The objects of the present invention can thus be achieved by a method for treating colostrum, which method is characterized by (a) collecting colostrum (b) defattening said colostrum (c) carrying out cross flow microfiltration (CFMF) of the defatted colostrum using a tangential flow filter (TFF) device with open channels, and a filter having a pore size of 0.1–0.5 μm, and (d) recovering the filtrate.

The colostrum of the present invention is characterized by being treated by the method of the invention.

The invention is further directed to the use of the treated colostrum for the manufacture of clinical nutritive preparations, functional foods, or food supplements comprising said colostrum.

DETAILED DESCRIPTION OF THE INVENTION

According to the method of the present invention colostrum is collected from a mammal, which can be any mammal e.g. goat or sheep, but preferably it is a cow. Preferably the mammal has previously been immunized or hyperimmunized against a pathogen, whereby colostrum useful for treating or preventing the disease caused by the pathogen can be obtained. The colostrum is collected soon after parturition, when the IgG content is at its maximum, usually within three days and preferably within 48 hours from parturition. The colostrum is normally, but not necessarily frozen and then cautiously thawed before processing, whereby high temperatures should be avoided. The fat is separated from the colostrum in any conventional way, usually by centrifugation. Preferably the obtained skim milk is then clarified for example by prefiltration through a depth filter or a membrane filter to remove possible clumps prior to the cross flow microfiltration step. Suitable filter media are e.g. polypropylene, regenerated cellulose or polyethersulfone having a pore size of 0,1–150 $\mu$m, normally about 0,5–50 $\mu$m.

Microfiltration (MF) is a pressure-driven separation process that uses membranes of a given pore size to separate components in a solution or suspension on the basis of their size difference. Although larger particles can be removed by use of non-membrane or depth filters, only a membrane filter having a precisely defined pore size can ensure quantitative retention. The conventional MF is a dead-end process, where the solution is vertically passed through the membrane. The particles which are too big to pass the pores are retained on the membrane surface, whereby the filter is quickly clogged. A development of MF is cross-flow microfiltration (CFMF), where the retained solution circulates tangentially across the membrane surface. Cross-flow is the rate at which the material flows across the membrane surface and is important as it generates a number of forces which tend to remove the deposited layers from the membrane surface thus helping to keep the membrane clean.

In cross flow microfiltration permeate or filtrate is the solution, which has passed through the membrane, retentate is the solution or suspension retained by the membrane and flux is the filtrate flow through the membrane.

The microfiltration of the defatted colostrum according to the present invention is carried out by cross flow microfiltration (CFMF) using a tangential flow filter (TFF) device. TFF membrane devices may be linear or turbulence promoted depending on the tangential flow channel design for material flow. So called open channel devices have straight, open feed flow channels, which allow a laminar flow in the channels, whereas the turbulence promoted so called thin channel devices have feed flow channels containing e.g. a screen, which promotes turbulence. The open channel devices should be used in the method of the present invention. TFF open channel devices may be obtained e.g. from Millipore Corp., Bedford, Mass., USA (Prostak™).

The membrane to be used in the open channel device is a flat sheet membrane, which has a pore size preventing bacteria and other microorganisms from passing to the filtrate, but allowing the desired proteins e.g. IgG to penetrate. A suitable pore size for this purpose is normally between 0.1–0.5 $\mu$m, and preferably 0.2–0.45 $\mu$m, especially about 0.2 $\mu$m. The filters can be e.g. polysulfone, cellulose, or especially fluorocarbon polymer based membranes. Polyvinylidene fluoride (PVDF) membranes are especially suitable for the CFMF of colostrum, and most preferred are PVDF membranes, which have been hydrophilized.

In order to increase the filter area and speed up the filtrate flux several filter device modules can be combined. Normally 100–200 liter colostrum is filtered with a capacity of 10–50 $l/m^2h$, preferably 20–40 $l/m^2h$ and especially about 25 $l/m^2h$ at a pressure of about 0.5–3 bar, preferably 0.8–2 bar and especially 1 bar. The filtrate containing the active proteins, but substantially free of any bacterial or other microbial contaminants, is recovered. Optionally the cross-flow microfiltered colostrum is finally sterile filtered by conventional microfiltration through a 0.2–0.45 $\mu$m membrane to ensure a sterile end product.

Often it is desirable to concentrate the filtered colostrum to enrich the proteins in question and optionally to remove salts. This can be done in a way known per se e.g. by ultrafiltration or reverse osmosis depending on the nature of the protein. It is finally possible to dry the filtered colostrum for example by lyophilization. Alternatively, the colostrum may be spray dried under controlled temperatures to avoid protein denaturation. The dried colostrum can either be e.g. encapsulated and used as such or dissolved in an aqueous solution before use.

In order to keep the microbial count low, the process should be carried out at low temperature. For the fat separation a temperature of about 40° C. is convenient, but the rest of the process is carried out at lower temperatures, preferably not exceeding 15° C., and mainly at a temperature of 2–10° C. Even at pumping during the CFMF, the temperature can be kept low and never allowed to exceed 40° C.

The method of the present invention may be used for different purposes where the aim is to obtain microbial free colostrum without substantial loss of valuable protein activities. Colostrum contains a lot of biologically active proteins such as hormones, growth factors, lactoferrin, bactericidal proteins and especially antibodies i.e. immunoglobulins of the classes IgG, IgA and IgM.

Colostrum of the present invention can be used in dry form or in the form of a beverage or food. It is especially suitable for the manufacture of clinical nutritive preparations, functional foods and food supplements comprising the treated colostrum. A clinical nutritive preparation is an article that is suitable for a person having special medical needs for the active components therein. Functional foods are foods having a health promoting effect, and food supplement is a food additive, which is added to give the food desirable properties. These products can conveniently be given orally to subjects in need thereof. IgG for example is useful in protecting mucous membranes against pathogen colonization and penetration, and it is especially suitable for treating or preventing enteropathogenic infections. The IgG rich, microbe free colostrum of the present invention may e.g. be given to immunosuppressed patients.

EXAMPLE 1

Dairy cows were immunized with formaline inactivated preparations of *Clostridium difficile* cells. A suspension of organisms in 0.5 ml of physiological saline was emulsified with 5 ml of aluminum hydroxide adjuvant. The resulting vaccine was administered intramuscularly in both sides of the cervical or shoulder five times during the last 8 weeks of gestation as follows: First injection: 2×4 ml, containing $10^9$ bacterial cells per 1ml vaccine; 1. and 2. boosters: 2×2 ml, containing $10^9$ bacterial cells per 1 ml vaccine; and 3. booster: 2×2 ml, containing 5×$10^8$ bacterial cells per 1 ml vaccine; and 4. booster: 2×2 ml, containing 2×$10^8$ bacterial cells per 1ml vaccine. Colostral milk was collected during the first two days of lactation. Colostral milk was frozen to −20 C. immediately after collection.

EXAMPLE 2

(a) Thawing of frozen colostrum 65 l of deep-frozen colostrum of immunized cows was placed into a thawing vessel with a blender and a mantle. The colostrum was heated to the separating temperature of 40° C.

(b) Separation of fat

Fat was removed from the colostrum obtained in step (a) with a separator resulting in 55 l skim milk. 50 ml lactase (BioFincon, GODO YNL) as added to hydrolyze the lactose present in the skim milk. Lactase enzyme as not removed at any point during the process.

(c) Clarification

The skim milk was prefiltered through a depth filter of polypropylene media (Millipore, Polygard 0.5 μm) to remove possible large particles from the skim milk. This step was expected to improve the performance of the actual CFMF. Prefiltered skim milk was transferred to the thawing vessel with a blender and a mantle and cooled to the CFMF temperature of 7–9° C.

(d) Cross flow microfiltration (CFMF)

Cooled skim milk was cross flow microfiltered through open channel filter modules having Durapore hydrophilic PVDF membranes on polysulfone plates, the membrane pore size was 0.22 μm and channel height approx. 0.5 mm (Millipore, Prostak™, GVPP). The skim milk was pumped to the open channel module at the pressure of 1 bar. The pumping capacity of the centrifugal pump was 100 l/min. No significant initial flux loss was observed during the cross flow microfiltration. 52.5 l of filtrate was recovered and the final temperature was 15° C. For comparison turbulence promoting thin channel filter modules with the same membranes (Millipore, Pellicon™, GVPP) were used.

(e) Results

A simple competitive enzyme linked immunosorbent assay (ELISA) was used to detect the immunoglobulin G (IgG) contained in the process fractions. The IgG recovery in the open channel CFMF process was 95% whereas the recovery from the thin channel CFMF process was only 30%.

Antibody titer i.e. the relative amount of biologically active vaccine-specific immunoglobulin in the process fractions was analyzed by using immobilized *C. difficile* cells as a solid phase in ELISA. The high titer (1:432,000) was retained constant during the process, which is in good correlation to the 95% recovery of the total IgG.

Total plate count was measured before and after the open channel CFMF step. The total plate count was reduced from $1.2 \times 10^6$ cfu/ml to less than $1.0 \times 10^1$ cfu/ml, or by 5.1 logs.

EXAMPLE 3

65 l of deep-frozen colostrum of non-immunized cows was defatted and processed according to the method described in Example 2 using the open channel devices (here also called the colostrum process). 45 l of filtrate as obtained. The IgG content was determined as described above. The results are shown in Table 1.

69 l of deep-frozen colostrum of non-immunized cows was placed into a thawing vessel with a blender and a mantle. The colostrum was heated to the separating temperature of 40° C. Fat was removed from the colostrum with a separator resulting in 61 skim milk. 50 ml lactase (BioFincon, GODO YNL) was added to hydrolyze the lactose present in the skim milk. Lactase enzyme was not removed at any point during the process. Rennet (Renco Rennet; Biofincon; 1:50000) was added to the skim milk at 32° C. and the cheese was cut after 30 min. Obtained cheese whey (52 l) was prefiltered through a depth filter (Millipore, Polygard, 0.5 μm) to remove possible large particles from the cheese whey. Prefiltration was meant to improve the performance of the actual CFMF step. Prefiltered whey was transferred to the thawing vessel and cooled to the CFMF temperature (7–9° C.). Cooled cheese whey was cross-flow microfiltered through open channel filter modules (Millipore, Prostak™, GVPP). Whey was pumped to the open channel module at 1 bar pressure with a centrifugal pump. The pump capacity was 100 l/min. 45 l of filtrate was recovered and the final temperature was 15° C. The IgG content was determined. The results are shown in Table 1.

TABLE 1

Comparison of the results in colostrum and cheese whey processes.

| Process material | Raw colostrum (non-immun.) | | Whey IgG | | Filtrate | | |
|---|---|---|---|---|---|---|---|
| | V [l] | IgG [g/l] | V [l] | [g/l] | V [l] | IgG [g/l] | [g] |
| Colostrum | 65 | 25.5 | — | — | 45 | 24.3 | 1093 |
| Cheese whey | 69 | 26.1 | 52 | 21.4 | 45 | 17.2 | 774 |

The amount of immunoglobulin G recovered in the cheese whey process was 30% less than in the colostrum process.

EXAMPLE 4

To compare the recovery of IgG as well as CFMF performance, test runs were made in laboratory scale with colostrum, acid whey and cheese hey. 1000 l of colostrum was firstly defatted and put into smaller containers and frozen to −20° C. Deep frozen defatted colostrum was rapidly thawed to 10° C. Acid whey was made by addition of HCl to the defatted colostrum to reduce the pH to 4.5 and the acid whey was removed by centrifugation. Rennet was added to heated defatted colostrum at 32° C., after which cheese whey was recovered after cutting the cheese.

The defatted colostrum, and the acid whey and cheese whey prepared therefrom were prefiltered through separate depth filters and the resulting solution was either processed as such, or diluted with ionized water 1:5 before CFMF with Millipore Prostak™ GVPP filter devices. A rotary lobe pump (Amicon) was used in said filtrations. The volume of the feed in each individual test run was 10 l, the pressure at the feed side was 0.9 bar. The results are shown in Table 2.

TABLE 2

Comparison of the results in colostrum, acid whey and cheese whey processes.

| Process material | Dilution | Flux [l/m²h] | $IgG_{feed}$ [g/l] | $IgG_{permeate}$ [g/l] | $IgG_{retentate}$ [g/l] | Permeability $(C_p/C_f)\%^*$ |
|---|---|---|---|---|---|---|
| Colostrum | no | 29.4 | 26.5 | 25.2 | 27.8 | 95 |
| Colostrum | 1:5 | 72.3 | 5.4 | 5.1 | 5.7 | 95 |

TABLE 2-continued

Comparison of the results in colostrum, acid whey and cheese whey processes.

| Process material | Dilution | Flux [l/m²h] | IgG$_{feed}$ [g/l] | IgG$_{permeate}$ [g/l] | IgG$_{retentate}$ [g/l] | Permeability (C$_p$/C$_f$)%* |
|---|---|---|---|---|---|---|
| Acid whey | no | 28.2 | 21.5 | 16.1 | 26.9 | 75 |
| Acid whey | 1:5 | 69.6 | 4.7 | 4.2 | 5.2 | 90 |
| Cheese whey | no | 22.6 | 19.7 | 15.8 | 23.6 | 80 |
| Cheese whey | 1:5 | 57.8 | 4.1 | 3.1 | 5.1 | 75 |

*$\frac{\text{Concentration in permeate}}{\text{Concentration in feed}} \times 100\%$ The actual permeate fluxes in both whey processes were worse than in the colostrum processes, so was the IgG permeability. Dilution of the colostrum improved permeate flux through the membranes by a factor of 2.5 while IgG was diluted by a factor of 5. Diluted IgG fractions need to be concentrated afterward, which increases process expenses, time and in addition there are post contamination possibilities.

EXAMPLE 5

20 l of cross flow microfiltered colostrum in example 2 was dead-end filtered with a 4" Millipore Opticap filter with Durapore™ PVDF media of 0.22 μm pore size under a laminar flow cabinet, and it was bottled aseptically into 500 ml bottles. The bottled product was absolutely sterile. The sterile dead-end filtration of colostrum was possible only after it was cross flow microfiltered through a membrane of the same pore size. Alternatively, a 4" Millipore Opticap filter with Milligard™ media (mixed esters of cellulose) of 0.22 μm pore size was used prior to bottling.

EXAMPLE 6

10 l of cross flow microfiltered colostrum in example 2 was successfully lyophilized without a need for further concentration to produce colostrum powder. The powder was later dissolved in water or phosphate buffered saline (0.1 M, pH 7.0).

We claim:

1. A method for treating colostrum to reduce the bioburden while retaining a high active protein content, said method comprising
   (a) collecting colostrum
   (b) defattening said colostrum
   (c) carrying out cross flow microfiltration (CFMF) of the defatted colostrum using a tangential flow filter (TFF) device with open channels, and a filter having a pore size of 0.1–0.5 μm, and
   (d) recovering the filtrate.
2. The method of claim 1 wherein the CFMF is carried out using a filter having a pore size of about 0.2 μm.
3. The method of claim 1 wherein the CFMF is carried out using a filter of hydrophilized polyvinylidene fluoride (PVDF) membrane.
4. The method of claim 1 wherein the colostrum is collected from a cow within 48 hours from calving.
5. The method of claim 1 further comprising clarifying the colostrum prior to the CFMF.
6. The method of further comprising carrying out sterile filtration through a filter having a pore size of 0.2–0.45 μm after the CFMF.
7. The method of claim 1 further comprising drying the recovered filtrate.
8. The method of claim 1 wherein the colostrum is collected from a mammal, which has been immunized.
9. The method of claim 1 wherein the CFMF step (c) is carried out at a temperature not exceeding 40° C.
10. The method of claim 9 wherein the CFMF step (c) is carried out at a temperature of maximum 15° C.
11. A method for treating colostrum, in the absence of the addition of a salt, acid or base, to reduce the bioburden while retaining a high active protein content, said method comprising the successive steps of:
    (a) collecting colostrum,
    (b) defattening said colostrum,
    (c) carrying out cross flow microfiltration (CFMF) of the defatted colostrum using a tangential flow filter (TFF) device with open channels, and a filter of hydrophilized polyvinylidene fluoride (PVDF) membrane having a pore size of 0.1–0.5 μm, and
    (d) recovering the filtrate.

* * * * *